United States Patent
Pouratian

(10) Patent No.: US 9,220,458 B2
(45) Date of Patent: Dec. 29, 2015

(54) METHOD FOR DEEP BRAIN STIMULATION TARGETING BASED ON BRAIN CONNECTIVITY

(71) Applicant: THE REGENTS OF THE UNIVERSITY OF CALIFORNIA, Oakland, CA (US)

(72) Inventor: Nader Pouratian, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/098,948

(22) Filed: Dec. 6, 2013

(65) Prior Publication Data

US 2014/0171779 A1 Jun. 19, 2014

Related U.S. Application Data

(63) Continuation of application No. 13/562,273, filed on Jul. 30, 2012, now abandoned.

(60) Provisional application No. 61/512,584, filed on Jul. 28, 2011.

(51) Int. Cl.
*A61N 1/36* (2006.01)
*A61B 5/00* (2006.01)
*A61N 1/05* (2006.01)

(52) U.S. Cl.
CPC ............ *A61B 5/4887* (2013.01); *A61N 1/3605* (2013.01); *A61N 1/36067* (2013.01); *A61N 1/0534* (2013.01)

(58) Field of Classification Search
CPC ... A61N 1/05; A61N 1/36139; A61N 1/0534; A61N 1/37247; A61N 1/36067; A61N 1/36125; A61N 1/36185; A61N 1/3606; A61N 1/36064; A61N 1/36082; A61N 1/36103; A61B 5/0042; A61B 5/0476; A61B 5/055; A61B 5/4094; A61B 5/4848
USPC ...................................... 607/45–48, 115–116
See application file for complete search history.

(56) References Cited

U.S. PATENT DOCUMENTS

2012/0165904 A1* 6/2012 Lee et al. ......................... 607/90

* cited by examiner

*Primary Examiner* — Rex R Holmes
(74) *Attorney, Agent, or Firm* — Morgan, Lewis & Bockius LLP

(57) ABSTRACT

Due to the lack of internal anatomic detail with traditional magnetic resonance imaging, preoperative stereotactic planning for the treatment of tremor usually relies on indirect targeting based on atlas-derived coordinates. To overcome such disadvantages, a method is provided that allows for deep brain stimulation targeting based on brain connectivity. For example, probabilistic tractography-based thalamic segmentation for deep brain stimulator (DBS) targeting is suitable for the treatment of tremor.

19 Claims, 6 Drawing Sheets

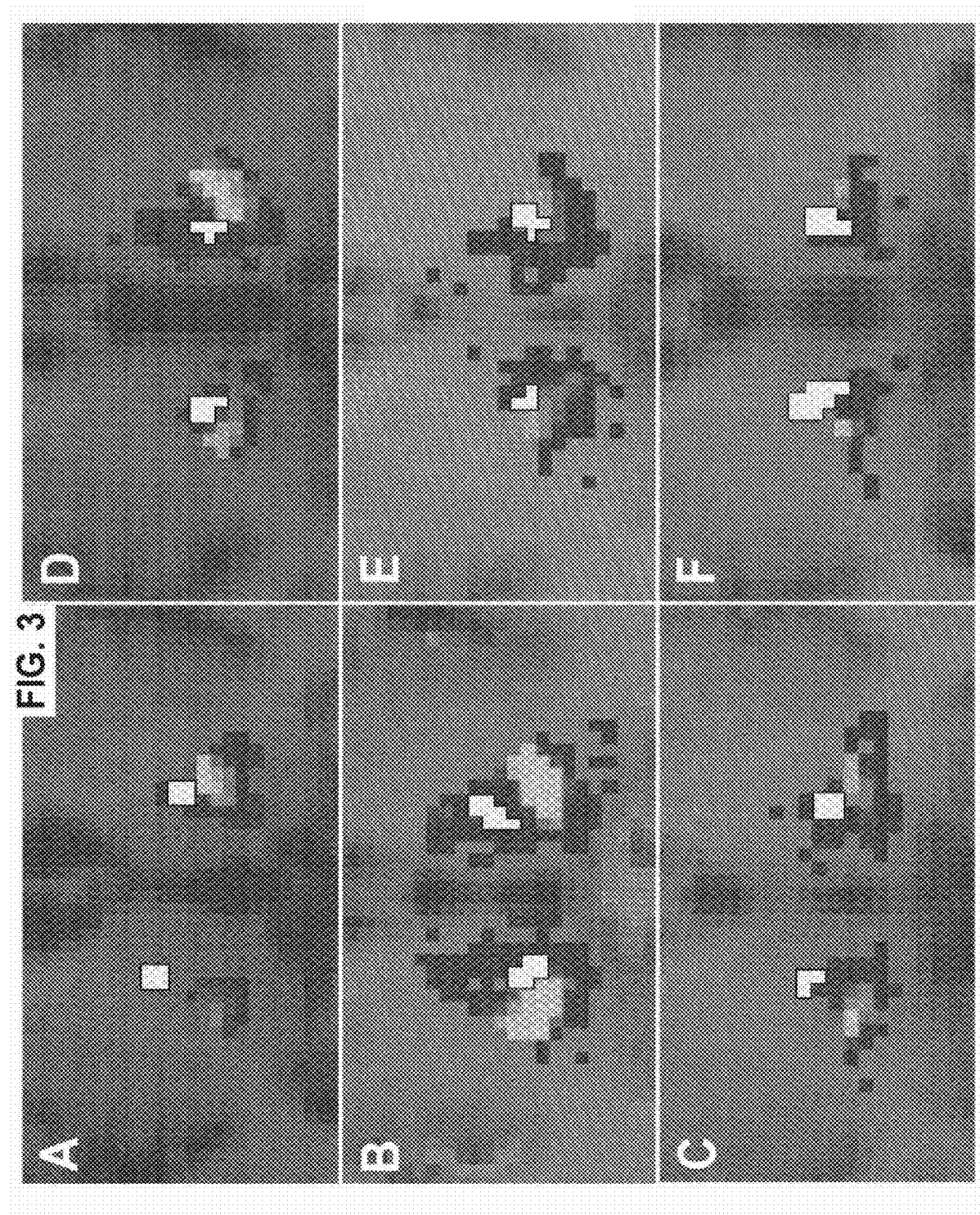

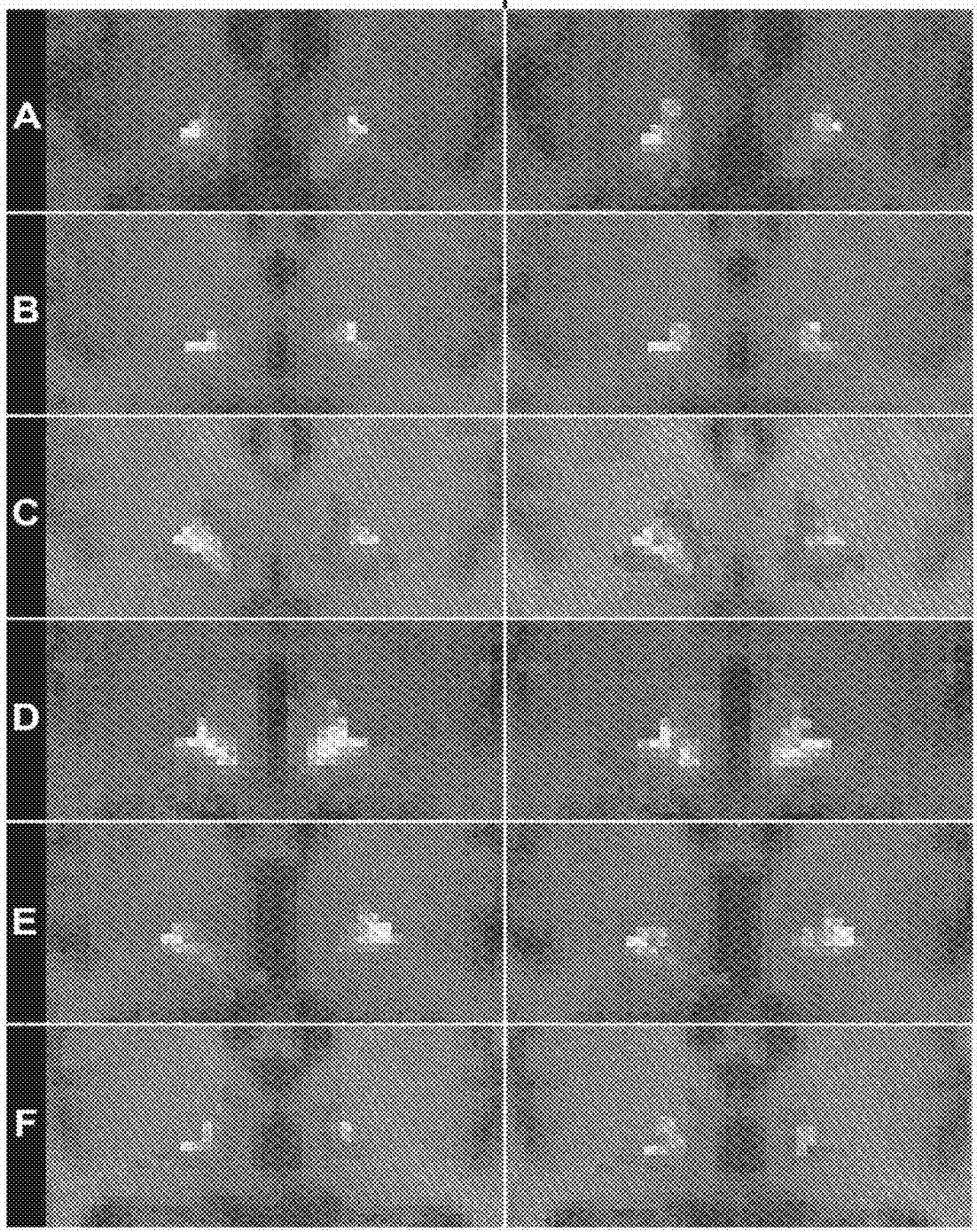

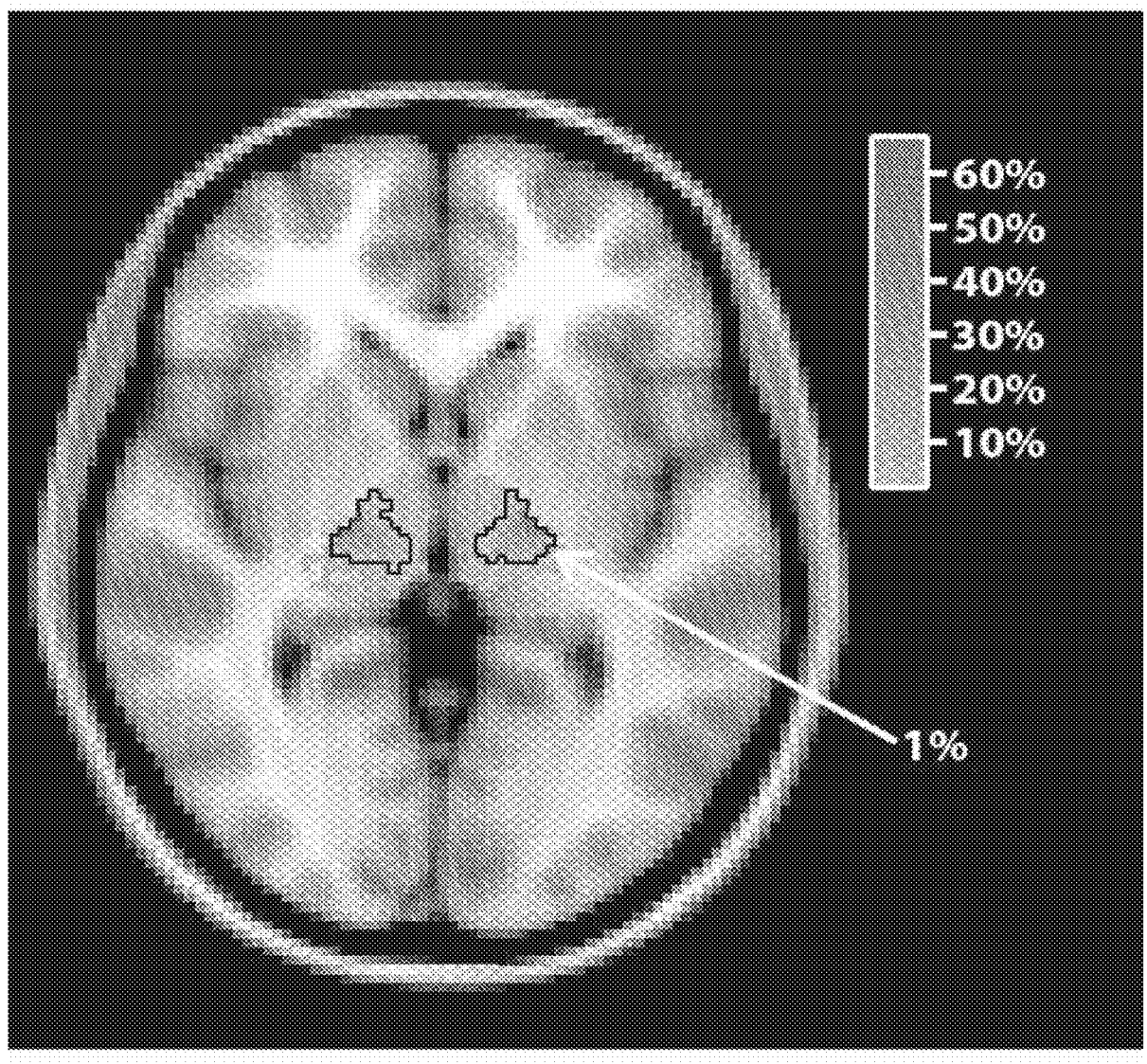

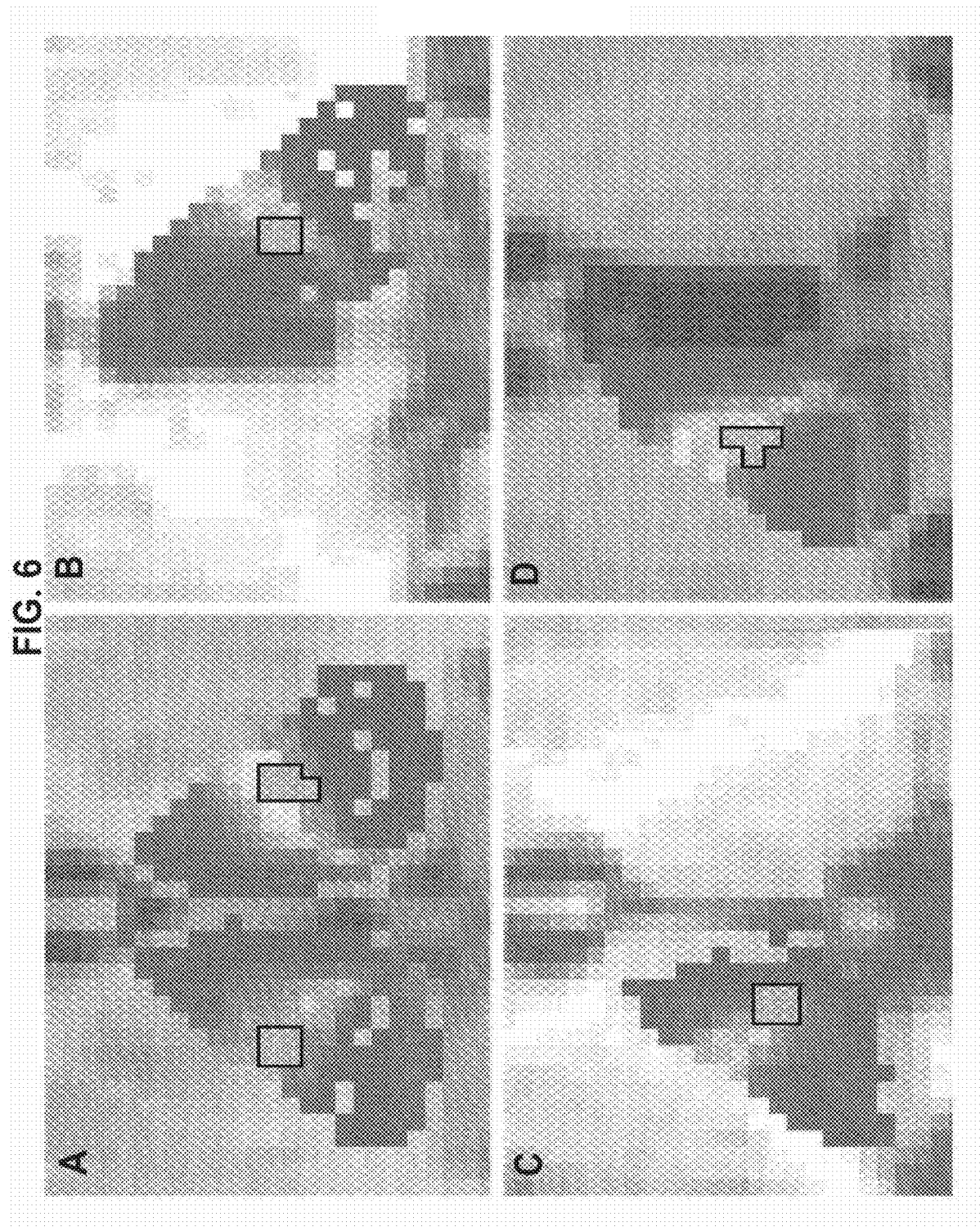

METHOD FOR DEEP BRAIN STIMULATION TARGETING BASED ON BRAIN CONNECTIVITY

CROSS-REFERENCES TO RELATED APPLICATIONS

This application is a Continuation of U.S. patent application Ser. No. 13/562,273 filed Jul. 30, 2012, entitled A METHOD FOR DEEP BRAIN STIMULATION TARGETING BASED ON BRAIN CONNECTIVITY (U.S. Patent Application Publication No. US 2013-0030499 A1), which claims priority to U.S. Provisional Patent Application No. 61/512,584 filed Jul. 28, 2011, entitled A METHOD FOR DEEP BRAIN STIMULATION TARGETING BASED ON BRAIN CONNECTIVITY, the entire contents of which is incorporated herein by this reference.

BACKGROUND OF INVENTION

1. Field of Invention

This application relates, in general, deep brain stimulation targeting based on brain connectivity and more particularly to methods of use.

2. Description of Related Art

The efficacy of deep brain stimulation (DBS) critically depends on accurate and precise targeting of subcortical targets. The lack of preoperative methods to either structurally or functionally delineate thalamic nuclear anatomy usually necessitates indirect targeting of the thalamus based on atlas-derived coordinates. Although indirect targeting of the thalamus is generally robust, variability in cortical and subcortical anatomy and function across individuals and across disease states would suggest that methods to identify patient-specific targets within the thalamus (or any other subcortical target) could enhance the safety and efficacy of DBS surgery.

The variability in anatomy and function of subcortical nuclei has been reported extensively in the functional neurosurgery and basic science literature. When targeting relative to the anterior and posterior commisures (AC and PC, respectively), efficacious targets for DBS are at best represented by a probability cloud of optimal electrode placement. Preoperative identification of a precise anatomical or physiological target is even more complicated in the thalamus where there are no readily visible nuclear boundaries that provide patient-specific details to guide targeting. Imaging and analysis techniques that can segment die thalamic nuclei can therefore aid in identifying patient-specific targets for DBS.

Prior studies have reported unique strategies for thalamic segmentation, including using spontaneous contrast and microscopic voxels in high-field magnetic resonance imaging (MRI) and using diffusion tensor magnetic resonance imaging (DTI) to evaluate characteristic fiber orientation of corticothalamic/thalamocortical striations within each thalamic nucleus. While these techniques are valid, their utility or reliability with respect to DBS targeting has not been evaluated. Moreover, in some cases, implementation of the described methodologies requires expertise and resources (e.g., 4.7 T MRI) that are not conventionally available to most physicians.

Based on the rationale that DBS likely exerts its efficacy by modulating activity at the network level, the present invention provides for connectivity-based segmentation of thalamic nuclei as a reliable and robust methodology for identifying optimal patient-specific targets for DBS electrode implantation. The importance of connectivity in mediating DBS efficacy was recently highlighted by optogenetic studies that implemented cortico-subthalamic projection fibers in the mechanism of efficacy of DBS of the subthalamic nucleus for Parkinson's disease. For example, it has been reported that using probabilistic diffusion tractography to identify thalamic subregions (i.e., nuclei) with unique patterns of cortical connectivity that were analogous to those previously described in histological and non-human primate studies and that were reproducible between individuals. Other reports have since provided functional-anatomic validation of thalamic segmentation using this approach and confirmed the reproducibility of the results. Such methodology has subsequently been used to segment other cortical, and deep brain targets, including but not limited to the substantia nigra, the subgenual cingulate, and the parietal cortex. Despite its increased application in the basic sciences, the value of using connectivity-based thalamic segmentation to guide DBS implantation has not been extensively evaluated.

In light of the foregoing, it would therefore be useful to provide a means of improving the precision of DBS targeting, in which connectivity-based analyses also can provide insight into the mechanisms and networks mediating DBS efficacy and overcome the above and other disadvantages of known methodologies. It would be useful to analyse optimal thalamic DBS electrode locations for tremor control in relation to patterns of connectivity-based thalamic segmentation in order to evaluate a patient-specific means of targeting DBS electrodes. It would be useful to conduct DTI-based analyses using available and easy-to-use image analysis software. And it would be useful to compare the variability of targeting relative to DTI-based maps to that seen with AC-PC reference frame and describe the variability in targeting across patients.

BRIEF SUMMARY

The present invention relates to neuromodulatlon, in particular deep brain stimulation, which has emerged as a major treatment modality for multiple neurological disorders including movement disorders. Clinical trials are underway for treatment of epilepsy and psychiatric disorders as well. Successful treatment relies on several factors including patient selection, precise targeting and surgical technique, and comprehensive postoperative programming. Targeting, or the methods for identifying where to place electrodes within the brain, are primarily based on structural or anatomic images and standardized atlases. In accordance with the present invention, application of a more precise and individualized method of defining brain structure and anatomy is based on brain connectivity. This methodology has been validated across two centers and targeting based on this method correlates with the therapeutic efficacy. Applying this methodology can have significant implications for targeting other new targets in the brain that have poor internal anatomical definition on standard imaging but may have important internal structure relevant to neuromodulation. Potential applications include the amygdala for treatment of psychiatric diseases and the hypothalamus for psychiatric and pain syndromes.

Based on the notion that deep brain stimulation achieves therapeutic efficacy by modulating brain networks, the present invention provides for a means of targeting deep brain stimulation electrodes based on brain connectivity patterns and measures. Although measures of brain connectivity using diffusion tensor imaging (DTI) and tractography have been previously described. In accordance with the present invention, this is the first description of using this methodology specifically to target brain structures for therapeutic brain stimulation. Likewise, this is the first demonstration that targeting brain structures based on these connectivity measures is actually precise and can account for interindividual variability. The described methodology is superior to prior methodologies because it (1) identifies targets based on individual anatomy and connectivity instead of relying on standard atlases and (2) can target therapeutic brain electrodes in regions of the brain in which there is normally insufficient contrast to identify internal structure.

In accordance with various aspects of the present invention, preoperative MRI with diffusion tensor imaging is obtained, a region of interest is defined for the target region, and the probability of connectivity of each voxel within the region of Interest with various and discreet remote brain regions are determined using an MRI analysis tool (e.g., FSL, a publicly available MRI analysis tool). Depending on the desired effect, the region within the ROI with the highest probability of connectivity with the desired remote brain region is selected as the target for deep brain stimulation targeting.

In accordance with various aspects of the present invention, patients undergoing deep brain stimulation undergo neuroimaging prior to surgery and implantation. The preoperative imaging protocol will be modified to include special sequences that can be used to analyze connectivity measures, specifically diffusion tensor imaging. These images may require preoperative analysis for defining optimal and efficacious targets for deep brain stimulation. Methodology for automation for brain stimulation targeting purposes may also be utilized in accordance with various aspects of the present invention.

The methods of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIGS. 3A-F illustrates efficacious contact position relative to thalamic M1 connectivity in accordance with the present invention.

FIGS. 4A-F illustrate efficacious contact for thalamic stimulation colocalizes with thalamix voxels with highest probability of connectivity with premoter and supplementary motor cortices in accordance with the present invention.

FIG. 5 illustrates variability of PMC connectivity across subjects in standard space.

FIGS. 6A-D illustrate external validation of colocalization of efficacious contacts and PMC-connectivity maps.

DETAILED DESCRIPTION

Figure 1:
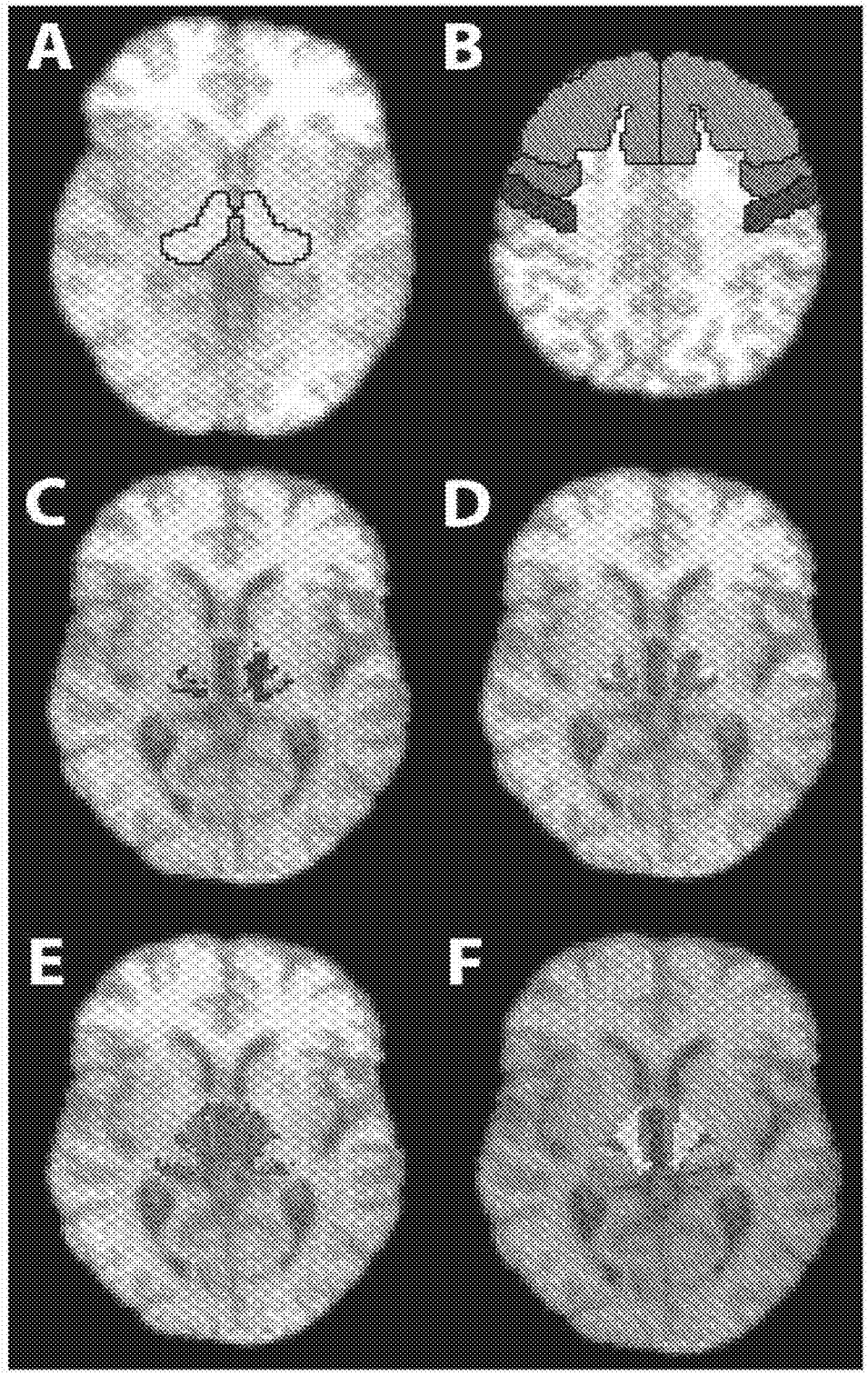
FIGS. 1A-F illustrate a method for connectivity-based thalamic segmentation in accordance with the present invention.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included, within the spirit and scope of the invention as defined by the appended claims.

By way of background, due to the lack of internal anatomic detail with traditional magnetic resonance imaging, preoperative stereotactic planning for the treatment of tremor usually relies on indirect targeting based on atlas-derived coordinates. In accordance with the present invention, probabilistic tractography-based thalamic segmentation for deep brain stimulator (DBS) targeting has been investigated for the treatment of tremor.

One study followed six patients undergoing bilateral implantation of deep brain stimulator electrodes in the thalamus for the treatment of upper extremity tremor. All patients underwent stereotactic surgical implantation using traditional methods (based on indirect targeting methodologies and intraoperative macrostimulation findings) and were programmed for optimal efficacy, independent of tractography-based segmentations described below. Connectivity-based thalamic segmentations were derived by identifying with which of seven cortical target regions each thalamic voxel had the highest probability of connectivity. The location of optimal contact for treatment of tremor with connectivity-based thalamic segmentations was retrospectively analyzed. Findings from one institution (University of California, Los Angeles "UCLA") were validated with results from four patients at another institution (University of Virginia, "UVA").

Of twelve electrodes implanted using traditional methodologies, all but one resulted in efficacious tremor control. Connectivity-based thalamic segmentation consistently revealed discrete thalamic regions with unique connectivity patterns with distinct cortical regions. Although initially hypothesized that the most efficacious DBS contact for controlling tremor would co-localize with the thalamic region most highly connected with primary motor cortex, it was instead found to highly co-localize with those thalamic voxels demonstrating a high probability of connectivity with premotor cortex (e.g., center-to-center distance: $0.36\,36\pm0.55$ mm). In contrast to the high degree of colocalization with optial stimulation site, the precise localization of the premotor cortex defined thalamic region relative to the anterior and posterior commisures was highly variable. Having defined a connectivity-based target for thalamic stimulation in a cohort of patients at UCLA, findings were validated in four patients (5 electrodes) operated on at a different institution (UVA) by a different surgeon.

The discussion below identifies and provides preliminary external validation of a novel means of targeting a patient-specific therapeutic thalamic target for the treatment of tremor based on individualized analysis of thalamic connectivity patterns. This novel thalamic targeting approach is based on identifying the thalamic region with the highest probability of connectivity with premotor and supplementary motor cortices. This approach may prove to advantageous over traditional preoperative methods of indirect targeting, providing patient-specific targets that could improve the precision, efficacy, and efficiency of deep brain stimulation surgery. Prospective evaluation and development of methodologies to make these analyses more widely available to neurosurgeons are likely warranted.

Methods

General Procedure

With reference to FIG. 1, using previously described methodology, the thalamus was segmented based on differential patterns of connectivity with seven predefined cortical targets. As shown in FIG. 1A, the thalamus was manually masked in each patient. As shown in FIG. 1B, cortical target masks were likewise delineated in each subject. In this figure the prefrontal (green), premotor (red), and primary motor cortex (blue) targets masks are depicted. As shown in FIGS. 1C, 1D and 1E, using probabilistic tractograpy, the probability of each thalamic voxel connecting with the cortical target masks is defined. Specifically, thalamic connectivity with primary motor (see FIG. 1C blue), premotor (see FIG. 1D, red-yellow), and prefrontal (see FIG. 1E, green) cortices are illustrated. As shown in FIG. 1F, once probabilistic patterns of connectivity with each cortical target has been defined, thalamic voxels are assigned to a group based on the region with which it has the highest probability of connection, resulting in thalamic segmentations reminiscent of previously published reports and known thalamic nuclear organisation.

Figure 2:
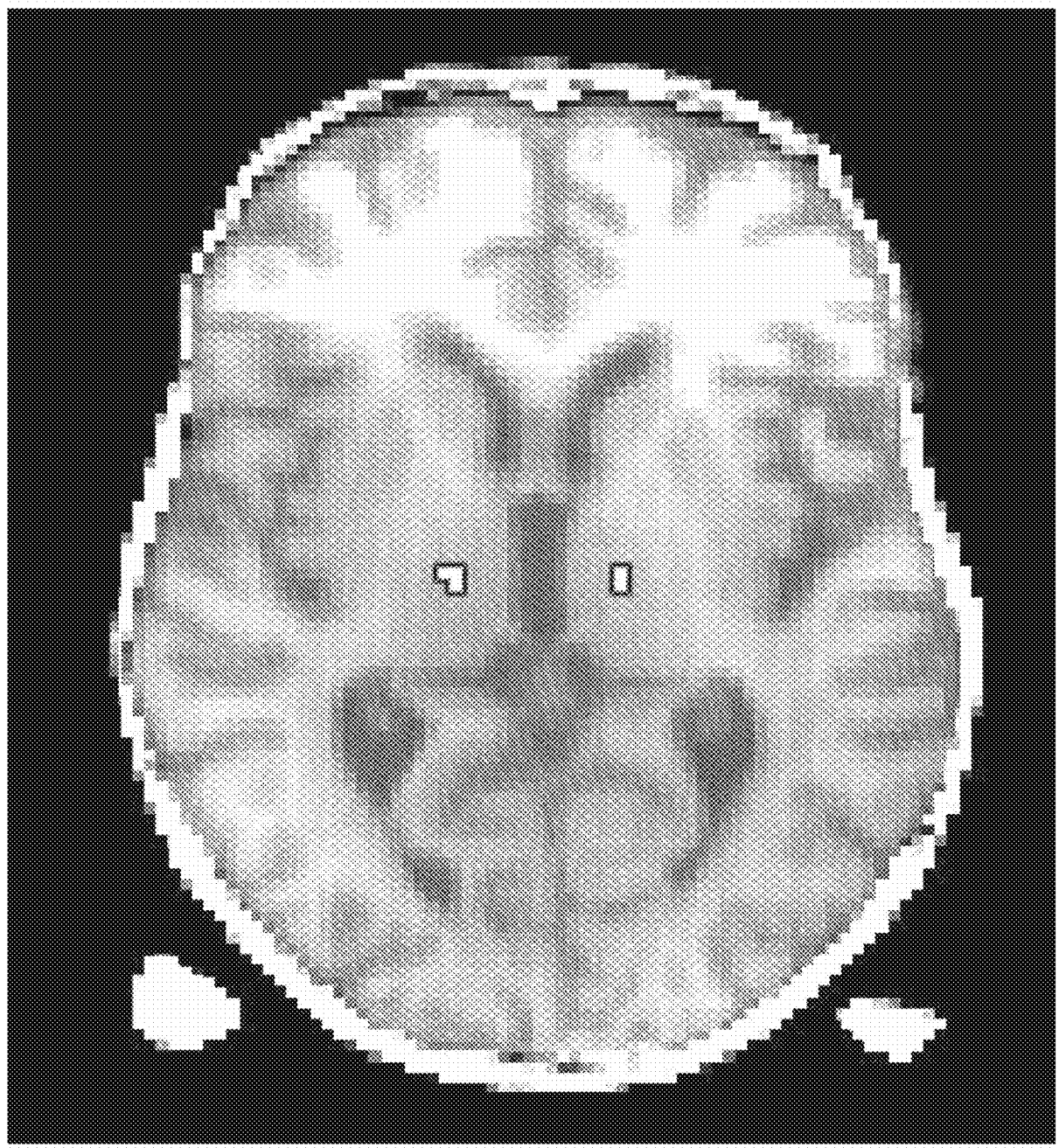
FIG. 2 illustrates image registration in accordance with the present invention.

With reference to FIG. 2, final electrode position after DBS implantation was determined by merging postoperative imaging (CT in this case) with the preoperative high-resolution T1-weighted MRI using a linear transformation. Connectivity based maps, illustrated in FIG. 1, were similarly merged into the high-resolution T1-weighted MRI space for intermodality comparisons.

With reference to FIG. 3, using probabilistic tractography, the probability of connectivity of each thalamic voxel with the anatomically defined primary motor cortex was determined. These probabilistic thalamic maps (blue overlays) and post-DBS implantation imaging (yellow overlays) were merged into a common space to compare relative position. Efficacious contact position (yellow color) is consistently anterior to those voxels with the highest probability of connectivity with the primary motor cortex flight blue=highest probability of M1 connectivity, dark blue=lower probability of M1 connectivity).

With reference to FIG. 4, using probabilistic tractography, the probability of connectivity of each thalamic voxel with the premotor cortex target mask (which includes lateral premotor and medical supplementary motor areas) was determined. These probabilistic thalamic maps (orange-yellow overlays) are illustrated for each subject (A-F) in the left column. Post-DBS implantation imaging (green overlays) were merged into a common space to compare relative position and plotted atop the thalamic probabilistic connectivity maps. Efficacious contact position (green color) is consistently colocalizes with those voxels with the highest probability of connectivity with the promoter cortex target mask (yellow=highest probability of PMC connectivity, red=lower probability of PMC connectivity).

With reference to FIG. 5, using affine transformation to account for intersubject anatomic variability, thalamic PMC-connectivity maps were transformed into a common apace, normalized, and averaged to assess the degree of intersubject spatial variability in PMC connectivity. Percentages denote an average normalized score of connectivity across subjects, where 100% would indicate consistent maximal spatial concordance with respect to thalamic connectivity with premotor/supplementary motor areas. The highest score is 60% suggesting significant intersubject variability in connectivity patterns even after anatomic differences are accounted for.

And with reference to FIG. 6, four subjects (6 electrodes) were evaluated from a similar dataset at UVA, demonstrating similar localization of efficacious contacts within thalamic areas with the highest probability of connectivity with the PMC cortical target mask.

Study Population

In accordance with the present invention, a series of six patients were studied who underwent bilateral implantation of DBS for upper extremity essential tremor at UCLA and who had DTI sequences included in their preoperatively obtained DBS planning MRI. Data from four additional patients from UVA who met similar criteria were also analyzed to validate the UCLA experience and findings. To avoid potential disease-specific differences in white-matter integrity and imaging characteristics which could complicate interpretation, only patients with essential tremor were included in the current analysis. Expedited institutional review was obtained for this retrospective analysis.

Image Acquisition

At both institutions, preoperative DBS planning MRI were acquired before the date of implantation. Sequences included a high-resolution T1-weighted anatomical sequence, namely TR 11 msec, TE 2.81 msec, flip angle 20°, matrix 256×256, field-of-view (FOV) 24 cm, and a slice thickness of 0.90 mm without a gap, resulting in a voxel size of 0.94×0.94×0.90 mm. Twenty-direction DTI was acquired using single-shot spin-echo echo-planar imaging with TR 9100 msec, TE 87 msec, matrix 128×128, FOV 25.6 cm, and a slice thickness of 2 mm with no gap, which analysis resulted in a voxel size of 2×2×2 mm. Diffusion-sensitizing gradient echo encoding was applied in 20 directions using a diffusion-weighted, factor b=1000 s/mm$^2$. One volume was acquired without use of a diffusion gradient (i.e., b=0 s/mm$^2$). The DTI imaging time was approximately 3:40 minutes.

Surgical Procedure

Methods for DBS implantation in the thalamus for treatment of tremor were similar at both institutions. The ventral intermediate (ViM) nucleus of the thalamus was targeted using indirect techniques relative to the anterior and posterior commisures (AC and PC, respectively) based on coordinates extracted from the Schaltenbrand-Wahren atlas. In each case, a region was targeted approximately 12-14 mm lateral of midline, approximately 7 mm (or 25% of the AC-PC length) in front of PC, and at the depth of the AC-PC line. Frame placement (Leksell model G stereotactic frame, Elekta A B, Stockholm, Sweden) was performed the morning of surgery with local anesthetic after which high-resolution computed tomography (CT) images were obtained. All electrodes were inserted through precoronal burr holes. To minimize cerebrospinal fluid (CSF) loss during electrode insertion, patients were maintained in a semi-recumbent position and the burr holes were occluded with Gelfoam or Tisseal. Microelectrode recordings (MER) were not conducted in any patients in this series. Implantations were performed without sedation to permit intraoperative macrostimulation to confirm optimal electrode position. Electrodes were moved in 2 mm increments when stimulation resulted in adverse effects at unacceptably low stimulation thresholds. Surgical implantation of DBS electrodes was done without knowledge of the thalamic segmentation results described in this report.

Defining Seed and Target Masks

Probabilistic connectivity-based thalamic segmentation requires delineating thalamic and cortical masks for each subject. Therefore, before proceeding with diffusion image analysis, individual masks for the thalamus and each cortical target region were defined on each subject's high-resolution T1-weighted MRI. Based on previous reports, one seed mask and seven cortical target masks were delineated for each subject in each hemisphere studied: thalamus (THAL, seed mask), prefrontal cortex (PFC), premotor and supplementary motor cortices (PMC), primary motor cortex (M1), primary somatosensory cortex (PSC), temporal cortices (TC), posterior parietal cortex (PPC), and occipital cortex (OC). The anatomic limits of these areas have been defined and published previously and are also available on the internet (http://www.fmrib.ox.ac.uk/connect/definitions.html). Cortical target masks defined in standard space (MNI-152) were initially transformed into each subject's T1-weighted high-resolution anatomic space using affine transformation. Using the reverse transformation of the transformation derived, each subject's anatomic MRI was aligned with MNI-152 standard atlas. FSLView was subsequently used to manually correct the masks for individual anatomic variability (see FIGS. 1A and 1B).

Diffusion Image Analysis

Probabilistic diffusion tractography was performed using methods previously described in detail using FSL tools, specifically the FMRIB's Diffusion Toolbox (FDT)(see http://www.fmrib.ox.ac.uk/fsl). FDT uses Bayesian techniques to estimate a probability distribution function (pdf) on the principal fibre direction at each voxel. Using these pdf the probability of connection between seed voxels (in the thalamus) and the predefined cortical targets described above could then be determined. The thalamus was then segmented into discrete nuclei on a voxel-by-voxel basis based on the cortical target with which each thalamic voxel is most dominantly connected. Details of these methods are briefly described.

Diffusion data were initially unwarped based on field map data using the eddy current correction tool within FDT and skull stripped using FSL's brain extraction tool (BET). Voxelwise estimates of fibre orientations and their uncertainty were then calculated using FDT with a model that accounts for the possibility of crossing fibres within each voxel (BEDPOSTX). The diffusion data were then registered (using linear registration, FLIRT) to the high-resolution T1-weighted image using the volume in which no diffusion gradient was applied. Utilizing the BEDPOSTX output, seed and target masks as defined in high-resolution T1-weighted space, and the transformation matrices to determine the probability of connectivity of each thalamic voxel, with each cortical target using PROBTRACKX (see FIGS. 1C-1F). Finally in order to generate a thalamic nuclear segmentation map, the "find_the_biggest" function was applied which classified each thalamic voxel according to the target mask with which it showed the highest probability of connection (sec FIG. 1F).

Postoperative Image Registration and Analysis

Final electrode position after DBS implantation was determined by obtaining a postoperative CT (UCLA) or anatomic MRI using an identical T1-weighted anatomical sequence (UVA) and merging these postoperative scans with the preoperative high-resolution T1-weighted MRI (FIG. 2). These fusion images were analyzed to determine whether the most efficacious contact consistently co-localized with a particular thalamic subregion (based on connectivity profile) and to determine the position of the electrode relative to AC-PC.

Clinical Assessment

The optimal contact for tremor suppression and clinical efficacy were retrospectively extracted from the medical record. Unfortunately, obtaining formal pre- and post-operative objective tremor ratings was not part of the regular clinical practice at UCLA. Therefore, as this image-based analysis is retrospective, formal tremor assessments scales were not available for detailed analysis. This may prove to be an important area for further investigation in future studies.

Results

Demographics and Clinical Outcomes

Six patients at UCLA (3 males, 3 females) underwent bilateral DBS implantation (12 total electrodes) for medically-refractory upper extremity essential tremor. Age at time of implant ranged from 61 to 82 years (median=66.5 years, mean=69.3 years). All but one electrode resulted in clinically meaningful tremor suppression which patients reported significantly improved their quality-of-life. Objective measures of pre- and post-operative tremor severity are not available as this was not part of the standard clinical protocol at UCLA at the lime of implantation. The four patients (5 electrodes) implanted at UVA included 3 males and 2 females.

Connectivity-Based Thalamic Segmentation

Connectivity-based thalamic segmentation consistently revealed discrete thalamic regions with unique connectivity patterns with distinct cortical regions (FIGS. 1C-F, 3, 4). The connectivity-based segmented thalamic nuclear architecture was topographically consistent with that previously reported in the literature and with known thalamic anatomy and connectivity (FIG. 1F).

Efficacious Contact Position Relative to Thalamic Segmentation

It was initially hypothesized that the most efficacious DBS contact for controlling tremor would co-localize with the thalamic region most highly connected to primary motor cortex (M1) because of literature suggesting primary motor cortex plays a role in tremor generation and DBS-mediated suppression (FIG. 3). However, direct comparison of motor-thalamus connectivity maps and the location of the optimal contact for tremor suppression revealed the contact location to be consistently and on average 1.8 mm (std dev=1.1 mm, minimum=0.5 mm, maximum=4 mm) anterior to the thalamic voxel with the most dominant primary motor cortex (M1) connectivity.

Because of the consistent anterior position of the optimal stimulation contact relative to the thalamic region most dominantly connected to M1, the hypothesis was secondarily tested that the efficacious contact would coincide spatially with the thalamic regions with dominant connections to promoter and supplementary motor areas (PMC). In cases of efficacious tremor control (all cases except the right-sided electrode illustrated in FIG. 4A), the optimal contact was directly within or directly adjacent to the PMC-thalamus (FIG. 4). In the anterior-posterior direction (i.e., Y), the mean center-to-center distance between contact and the most dominant PMC-connected thalamic voxel was 0.36±0.55 mm (min=0 mm, max=1.5 mm). In the medial-lateral direction (i.e, X), all efficacious contacts except for one (left-sided electrode in FIG. 4E) coincided with the medial most aspect of the thalamic voxels most dominantly connected to PMC. One electrode did not ultimately result in efficacious tremor control (FIG. 4A, right sided electrode) which is clearly anterior to the thalamic region with the highest probability of PMC-connectivity.

Anatomic Variability of DBS Target

To better appreciate the variability across subjects of this putative connectivity-based thalamic target for tremor suppression, an affine transformation was used to merge each subject's thalamic-PMC connectivity map into a common standard space (MNI-152). To provide a voxel-by-voxel estimate of "strength" of connectivity with the PMC target, each subject's map was normalized relative to the voxel with the highest PMC connectivity for that subject. These individual maps were then averaged in standard space; an average value near 100% would imply internal consistency in thalamic nuclear organization across subjects whereas increasingly lower values would imply decreasing intersubject consistency in location of voxels with dominant PMC connectivity (even after affine transformation that accounts for intersubject anatomic variability) (see FIG. 5). While the region of highest connectivity is relatively focal suggesting some internal consistency in thalamic organization (as would be expected), the maps are notable for having a maximum average PMC-connectivity weight at any particular voxel in standard space of 60%, implying there is not a single precise thalamic location or target that consistently demonstrates "strong" connections with the PMC target across subjects. The area with highest probability of connectivity with premotor thalamus in average space corresponded to 14 mm lateral of AC-PC and 8 mm (or 28.5% of the AC-PC length) in front of PC. The connectivity-based target relative to AC-PC for each subject/electrode at UCLA is reported in Table 1, below.

TABLE 1

Connectivity-based Thalamic Tremor Target relative to AC-PC

| | | Lateral Distance | Distance in front of PC | Posterior-Inferior |
|---|---|---|---|---|
| 1 | R | 14 mm | 8 mm | 0 mm |
| | L | 16 mm | 8 mm | 0 mm |
| 2 | R | 12 mm | 10 mm | 2 mm |
| | L | 16 mm | 12 mm | 4 mm |
| 3 | R | 14 mm | 8 mm | 2 mm |
| | L | 14 mm | 8 mm | 0 mm |
| 4 | R | 12 mm | 6 mm | 0 mm |
| | L | 12 mm | 6 mm | 0 mm |
| 5 | R | 14 mm | 6 mm | 2 mm |
| | L | 14 mm | 8 mm | 2 mm |
| 6 | R | 16 mm | 6 mm | 2 mm |
| | L | 14 mm | 8 mm | 2 mm |

To further characterize the variability in efficacious thalamic contacts for tremor suppression, the position of the efficacious contacts relative to AC and PC was evaluated. Although all electrodes were targeted to be on average 25.6±2.4% of the length of AC-PC in front of PC (min=23.4%, max=31.9%), the position of the efficacious contact on follow-up imaging were on average 29.0±6.6% of the length of AC-PC in front of PC (min=17.0%, max=39.5%). Relative to planned targets, the final contact positions demonstrate much greater variability both with respect to standard deviation and the range of positions. The final efficacious contact positions also notably demonstrate much greater variability than that seen relative to the DTI-based PMC-connectivity maps.

Validation of Connectivity-Based Thalamic Targeting with External Data

To validate the current preliminary findings, similar data was analyzed from UVA, which were collected blind of the current results. This analysis similarly revealed that the most efficacious contact consistently co-localized with the thalamic voxels having the highest probability of connection to the PMC target (FIG. 6).

Discussion

Using methods that are widely available and implementable and whose reproducibility and functional correlation have been previously validated, the present invention provides a connectivity-based approach for individualized thalamic segmentation and DBS targeting that is consistent across subjects and institutions and demonstrates less intersubject variability than classic indirect approaches. The limitations of indirect DBS targeting using atlas-based coordinates have long been recognized due to the limited dataset on which atlas are created and extensive intersubject anatomic and functional variability. There has therefore been a significant emphasis on developing superior imaging techniques and sequence parameters to improve direct targeting (or targeting based on targets visualized on an individual subject's MRI). While most imaging investigations and advances have focused on means to delineate the borders or margins of deep brain targets, few have explored methods to delineate the internal architecture of these structures. The handful of methods that have attempted to segment deep brain nuclei based on unique imaging characteristics have reported impressive results but have limited widespread application because they employ methodologies or neuroimaging expertise that are not widely available.

Connectivity-based segmentation provides an accessible and reliable means to Identify specific regions of interest within deep grey structures to be targeted for DBS. The approach is unique and theoretically preferable because it not only relies on unique intrinsic imaging characteristics of the distinct subregions of the thalamus but also accounts for the network or connectivity-based mechanism by which DBS is hypothesized to mediate its effects. Rather than using a finite seed-based approach to tractography in which the tracts generated are highly susceptible to the precise location and size of the seed selected, the current approach employs a probabilistic approach to defining the connectivity of the thalamus with multiple predefined cortical regions and uses this information to define distinct thalamic subregions. The consistent findings across institutions with two different surgeons (AAD and WJE) and different programmers (all of whom were blind of the current analyses) suggests that the current findings are not an artifact of institutional bias or techniques but a critical biomarker for thalamic stimulation to achieve effective tremor control.

Consistent with previous literature on intersubject variability in thalamic anatomy and sites of efficacious stimulation, the analysis of DTI-based thalamic segmentation and ACPC based locations of efficacious stimulation in this study confirms significant variability in thalamic anatomy and function across subjects and the need for methods to account for this individual variability when planning stereotactic surgery. While the current analysis is limited to that of the thalamic site of stimulation for tremor control, this method can and should be extrapolated to other deep brain targets in order to enhance the precision and efficacy of stimulation of distinct nuclear subregions within the globus pallidus, subthalamic nucleus, and other putative targets. Although the substantia nigra is not a target for DBS, the power of this approach to segment small deep grey structures has recently been highlighted in a report using probabilistic tractography to delineate the distinct parts of the substantia nigra.

Mechanistic Insights

A connectivity-based approach was employed and evaluated because of the increased recognition that DBS likely mediates its effects by modulating the interaction between cortical and subcortical networks. Using probabilistic tractography to segment the thalamus therefore acknowledges and incorporates a mechanistic view of DBS. This methodology has been used previously to evaluate the anatomic connectivity of the subgenual cingulate region and to support the hypothesis that DBS of the subgenual cingulate in treatment resistant depression is mediated by effects on a distributed network of frontal, limbic, and visceromotor brain regions.

It was originally hypothesized that the efficacious contact would co-localize with that part of the thalamus with the highest probability of anatomical connections with M1 because of the interconnectivity of ViM thalamus (the presumed target) with M1 and numerous reports of primary motor cortex modulation by DBS of the thalamus for tremor control. Nonetheless, analysis of data from two different institutions revealed that the site of efficacious stimulation colocalizes precisely with the thalamic region with the highest likelihood of connectivity with the PMC target, which includes both the lateral premotor cortices and the medial supplementary motor areas (FIGS. 4 and 6), rather than primary motor cortex (M1). The discrepancy may in part be due to the limited spatial resolution of previous studies which used PET to assess cortical modulation and attributed changes in the precentral gyrus to M1 modulation. The anterior and posterior banks of the precentral gyrus were segregated into premotor and primary motor cortex, respectively. Previous reports support a role of premotor and supplementary motor regions in modulating motor activity and being modulated in the setting of DBS for tremor control. While the current analysis and results clearly demonstrate an anterior displacement of the efficacious contact relative to the thalamic region with the strongest M1 connectivity (FIG. 3), given the center-to-center distance of contact to the region of the thalamus with dominant M1 connectivity is on the order of 2 mm which is the same as the current resolution of DTI (2 mm), it is likely that stimulation still modulates thalamocortical fibres projecting directly to M1. Nevertheless, the current results suggest that electrode placement in a region with strong PMC connectivity (including premotor and supplementary motor areas) may be advantageous. Based on these results, it is hypothesize that thalamic DBS efficacy is mediated by modulation of pathologic thalamocortical electrophysiological activity (i.e., rhythms) between thalamus and premotor and supplementary motor areas, rather than primary, direct modulation of the primary motor cortex. These results highlight the fact that the precise mechanisms of tremor control mediated by thalamic DBS are still incompletely understood.

Limitations and Future Directions

While thalamic targeting and stimulation are rather robust and may be perceived to not require additional methods for precise targeting, the current results provide a proof of principle and further the conclusions of a previous report that connectivity-based targeting may improve the efficacy of DBS therapy. Despite the striking results, the enthusiasm for the current results is tempered by the fact that this analysis is retrospective and is therefore susceptible to unforeseen patterns of bias. A prospective evaluation with formal objective pre- and postoperative evaluation of tremor is required to validate this approach for DBS targeting. Future investigations may precisely characterize the cortical target mediating DBS efficacy (i.e., premotor vs. supplementary motor areas). This prospective evaluation will have to closely assess the impact of standard DTI resolution (2 mm) on stereotactic planning, precision, and accuracy and determine whether high-resolution (≤1 mm) is clinically necessary or advantageous. Should the technique grave useful, reliable, and validated, measures will need, to be taken to automate the described methodology, including automated mask generation (seeds and targets) and streamlining of the code so that minimal user interface is required (using an environment such as the LONI pipeline) and clinical translation is possible.

CONCLUSIONS

Advances in neuroimaging require neurosurgeons to continuously re-evaluate the methodologies to delineate and target structure and function in the brain. Probabilistic tractography provides a reliable and seemingly precise approach to target finite regions of the thalamus to achieve therapeutic tremor control with DBS. This preliminary report suggests DBS efficacy is mediated by stimulating thalamic regions with the highest probability of interconnectivity with premotor and supplementary motor cortices. This connectivity-based analysis reveals internal anatomy that is not available with conventional imaging yet is easily obtained with widely available imaging processing tools. This method accounts for individual variability rather than relying on atlas-based (indirect) targeting, which is recognized as imperfect. Further validation with prospective analyses and investigation with other deep brain targets is warranted.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method for brain stimulation targeting based on brain connectivity, the method comprising:
   using an MRI system, acquiring a preoperative image of a brain;
   using image analysis software, defining a region of interest (ROI) of a brain in the preoperative image of the brain, the ROI including a plurality of voxels;
   using image analysis software, determining a probability of connectivity for each voxel in the plurality of voxels within the ROI with respect to each of a plurality of predefined target regions, wherein the determining of the probability of connectivity is conducted using diffusion tractography; and
   using image analysis software, segmenting the ROI to produce a connectivity map of the ROI with respect to a desired predefined target region in the plurality of predefined target regions, wherein
   the segmenting of the ROI is based on with which of the plurality of predefined target regions each voxel in the plurality of voxels within the ROI has the highest probability of connectivity, and
   the connectivity map provides an optimal location in the brain for directing stimulation with respect to the desired predefined target region in the plurality of predefined target regions.

2. The method of claim 1, further comprising:
   processing the preoperative image of the brain, prior to the defining of the ROI, to estimate fibre orientations voxelwise and calculates uncertainty of the estimated fibre orientations by taking into consideration of possibility of crossing fibres within each voxel.

3. The method of claim 1, further comprising:
   displaying the segmented ROI with the optimal location highlighted for a desired predefined target region in the plurality of predefined target regions.

4. The method of claim 1, further comprising:
   displaying the segmented ROI with the optimal location highlighted for each of the plurality of predefined target regions.

5. The method of claim 1, further comprising:
   obtaining a postoperative image after directing stimulation in the optimal location in the brain; and
   analyzing the postoperative image for accessing efficacy of the stimulation with respect to a desired effect.

6. The method of claim 1, wherein the preoperative image of a brain includes preoperative imaging.

7. The method of claim 1, wherein the defining of the ROI is conducted using a mask.

8. The method of claim 1, wherein the ROI includes a cortical or a subcortical structure of the brain.

9. The method of claim 1, wherein the ROI is thalamus, prefrontal cortex, premotor cortex, supplementary motor cortex, primary motor cortex, primary somatosensory cortex, temporal cortices, posterior parietal cortex, or occipital cortex.

10. The method of claim 1, wherein each of the plurality of predefined target regions is delineated by a mask.

11. The method of claim 1, wherein the plurality of predefined target regions includes thalamus, prefrontal cortex, premotor cortex, supplementary motor cortex, primary motor cortex, primary somatosensory cortex, temporal cortices, posterior parietal cortex, occipital cortex, or any combination thereof.

12. The method of claim 1, wherein the plurality of predefined target regions includes 2, 3, 4, 5 or more discrete regions.

13. The method of claim 1, wherein the diffusion tractography is performed using a FMRIB's Diffusion Toolbox.

14. The method of claim 1, wherein the segmenting of the ROI produces a connectivity map of the ROI with respect to each of the plurality of predefined target regions.

15. The method of claim 1, wherein the segmenting of the ROI is conducted on a voxel-by-voxel basis and corresponding to a desired effect.

16. The method of claim 1, wherein the optimal location in the brain is for implanting one or more stimulators for neuromodulation.

17. The method of claim 16, wherein the one or more stimulators includes an electrode.

18. A method for brain stimulation targeting based on brain connectivity, the method comprising:
    using an MRI system, acquiring a preoperative image of a brain;
    using image analysis software, defining a region of interest (ROI) of a brain in a preoperative image of the brain, the ROI including a plurality of voxels;
    using image analysis software, determining a probability of connectivity for each voxel in the plurality of voxels within the ROI with respect to each of a plurality of predefined target regions, wherein the determining of the probability of connectivity is conducted using diffusion tractography; and
    using image analysis software, segmenting the ROI into a plurality of groups, wherein
    a respective group in the plurality of groups includes voxels, each of which has the highest probability of connectivity with respect to a corresponding predefined target region in the plurality of predefined target regions, and
    the respective group in the plurality of groups provides an optimal location in the brain for directing stimulation with respect to the corresponding predefined target region in the plurality of predefined target regions.

19. A method for brain stimulation targeting based on brain connectivity, the method comprising:
    using an MRI system, obtaining a preoperative image of a brain;
    using image analysis software, defining, in the preoperative image of the brain, a region of interest (ROI) and a plurality of predefined target regions, wherein the ROI includes a plurality of voxels;
    using image analysis software, determining a probability of connectivity for each voxel in the plurality of voxels within the ROI with respect to each of the plurality of predefined target regions, wherein the determining of the probability of connectivity is conducted using probabilistic diffusion tractography;
    using image analysis software, segmenting the ROI on a voxel-by-voxel basis in terms of the determined probability with respect to a desired predefined target region in the plurality of predefined target regions, thereby producing a connectivity map of the ROI with respect to the desired predefined region to facilitate neuromodulation.

* * * * *